(12) United States Patent
Lee et al.

(10) Patent No.: US 12,600,939 B2
(45) Date of Patent: Apr. 14, 2026

(54) **MUTANT OF *CORYNEBACTERIUM GLUTAMICUM* WITH ENHANCED L-GLUTAMIC ACID PRODUCTIVITY AND METHOD FOR PREPARING L-GLUTAMIC ACID USING THE SAME**

(71) Applicant: DAESANG CORPORATION, Seoul (KR)

(72) Inventors: Young Ju Lee, Seoul (KR); Bong Ki Kim, Seoul (KR); Min Jin Choi, Gyeonggi-do (KR); Seok Hyun Park, Gyeonggi-do (KR); Jae Chun Han, Seoul (KR)

(73) Assignee: DAESANG CORPORATION, Seoul (KR)

( * ) Notice: Subject to any disclaimer, the term of this patent is extended or adjusted under 35 U.S.C. 154(b) by 129 days.

(21) Appl. No.: 17/798,792

(22) PCT Filed: Aug. 26, 2020

(86) PCT No.: PCT/KR2020/011406
§ 371 (c)(1),
(2) Date: Aug. 10, 2022

(87) PCT Pub. No.: WO2021/162189

PCT Pub. Date: Aug. 19, 2021

(65) Prior Publication Data

US 2023/0136217 A1     May 4, 2023

(30) Foreign Application Priority Data

Feb. 12, 2020     (KR) ........................ 10-2020-0017264
Aug. 21, 2020     (KR) ........................ 10-2020-0105435

(51) Int. Cl.
*C12N 1/20*          (2006.01)
*C07K 14/34*        (2006.01)
(Continued)

(52) U.S. Cl.
CPC ................ *C12N 1/20* (2013.01); *C07K 14/34* (2013.01); *C12N 15/67* (2013.01); *C12N 15/77* (2013.01); *C12P 13/14* (2013.01); *C12R 2001/15* (2021.05)

(58) Field of Classification Search
CPC .......... C12N 1/20; C12N 15/67; C12N 15/77; C07K 14/34; C12P 13/14; C12R 2001/15
See application file for complete search history.

(56) References Cited

U.S. PATENT DOCUMENTS

| | | | |
|---|---|---|---|
| 6,852,516 B2 | 2/2005 | Hibino et al. | |
| 6,962,805 B2 | 11/2005 | Asakura et al. | |
| 2006/0141588 A1* | 6/2006 | Nakamura | .............. C12P 13/14 |
| | | | 435/252.3 |

FOREIGN PATENT DOCUMENTS

| | | |
|---|---|---|
| CN | 108250278 | 7/2018 |
| JP | 2007-97573 | 4/2007 |

(Continued)

OTHER PUBLICATIONS

Nakayama et al. "Force-From-Lipids" mechanosensation in Corynebacterium glutamicum, May 4, 2019, Biophysical Reviews, vol. 11, p. 327-333. (Year: 2019).*

(Continued)

*Primary Examiner* — Vanessa L. Ford
*Assistant Examiner* — Amelia Nicole Dickens
(74) *Attorney, Agent, or Firm* — Wenderoth, Lind & Ponack, L.L.P.

(57) ABSTRACT

The present invention relates to a *Corynebacterium glutamicum* mutant strain having increased L-glutamic acid productivity, a method for constructing the same, and a method of producing L-glutamic acid using the same. The *Corynebacterium glutamicum* mutant strain is a strain into which a mechanosensitive ion channel gene derived from a *Corynebacterium* sp. strain has been introduced, and thus it can (Continued)

produce L-glutamic acid in an improved yield due to enhancement of glutamic acid release. Therefore, when the mutant strain is used, it is possible to more effectively produce L-glutamic acid.

3 Claims, 2 Drawing Sheets

Specification includes a Sequence Listing.

(51) Int. Cl.

| | | |
|---|---|---|
| *C12N 15/67* | (2006.01) | |
| *C12N 15/77* | (2006.01) | |
| *C12P 13/14* | (2006.01) | |
| *C12R 1/15* | (2006.01) | |

(56) References Cited

FOREIGN PATENT DOCUMENTS

| | | |
|---|---|---|
| JP | 2010-506585 | 3/2010 |
| JP | 2018-174717 | 11/2018 |
| KR | 10-0824457 | 4/2008 |
| KR | 102 075 160 | 2/2020 |
| WO | 2006/070944 | 7/2006 |
| WO | 2014/185430 | 11/2014 |

OTHER PUBLICATIONS

Persicke et al. "Genome sequence of the soil bacterium Corynebacterium callunae type strain DSM 20147T", 2015, Standards in Genomic Sciences, vol. 10, Article 5, p. 1-7. (Year: 2015).*

Pfeifer et al. "Adaptive laboratory evolution of Corynebacterium glutamicum towards higher growth rates on glucose minimal medium", Dec. 1, 2017, Scientific Reports, vol. 7, Article 16780, p. 1-14 (Year: 2017).*

Notice of Reasons for Refusal issued Aug. 14, 2023 in Japanese Application No. 2022-548767 (with English translation).

Accession No. WP_053544706, mechanosensitive ion channel family protein [Corynebacterium deserti], Database GenPept [online], 2017, [Retrieved on Aug. 4, 2023], Internet <URL: https://www.ncbi.nlm.nih.gov/protein/924865718?sat=54&satkey=16039145.

Accession No. CP009220, Corynebacterium deserti GIMN1.010, complete genome. Database GenBank [online], 2015, [Retrieved on Aug. 4, 2023], Internet <URL: https://www.ncbi.nlm.nih.gov/nuccore/CP009220.

Accession No. WP_066565323, mechanosensitive ion channel family protein [Corynebacterium crudilactis]Database GenPept [online], 2017, [Retrieved Aug. 4, 2023], Internet <URL: https://www.ncbi.nlm.nih.gov/protein/1054802338?sat=54&satkey=16375948.

Accession No. CP015622, Corynebacterium crudilactis strain JZ16 chromosome, complete genome. Database GenBank [online], 2017, [Retrieved on Aug. 4, 2023], Internet <URL: https://www.ncbi.nlm.nih.gov/nuccore/CP015622.

Accession No. WP_15651054, mechanosensitive ion channel family protein [Corynebacterium callunae], Database GenPept [online], 2017, [Retrieved on Aug. 4, 2023], Internet <URL: https://www.ncbi.nlm.nih.gov/protein/505464163?sat=54&satkey=15250405.

Decision of Refusal issued Jan. 15, 2024 in Japanese Application No. 2022-548767 (with English translation).

International Search Report issued Dec. 17, 2020 in International (PCT) Application No. PCT/KR2020/011406.

Corynebacterium callunae DSM 20147, complete genome, GenBank: CP004354.1, Jan. 16, 2015.

Nakayama, Yoshitaka et al., "*Corynebacterium glutamicum* mechanosensitive channels: towards unpuzzling "glutamate efflux" for amino acid production", Biophysical Reviews, published online: Sep. 12, 2018, vol. 10, pp. 1359-1369.

Nakamura, Jun et al., "Mutations of the *Corynebacterium glutamicum* NCgl1221 Gene, Encoding a Mechanosensitive Channel Homolog, Induce $_L$-Glutamic Acid Production", Applied and Environmental Microbiology, Jul. 2007, vol. 73, No. 14, pp. 4491-4498.

Extended European Search Report issued Feb. 1, 2024 in corresponding European Patent Application No. 20918924.0.

Junko Ohnishi et al., "A novel *gnd* mutation leading to increased $_L$-lysine production in *Corynebacterium glutamicum*", FEMS Microbiology Letters, vol. 242 (2005), pp. 265-274.

Marie-Antoinette Lanéelle et al., "Current knowledge on mycolic acids in *Corynebacterium glutamicum* and their relevance for biotechnological processes", Applied Microbiology Biotechnology (2013), vol. 97, pp. 9923-9930.

* cited by examiner

MUTANT OF *CORYNEBACTERIUM GLUTAMICUM* WITH ENHANCED L-GLUTAMIC ACID PRODUCTIVITY AND METHOD FOR PREPARING L-GLUTAMIC ACID USING THE SAME

REFERENCE BY INCORPORATION OF SEQUENCE LISTING

A sequence listing in electronic format is filed with this application and incorporated herein by reference in its entirety. The name of the file is "AttachB-SEQLIST-1573.txt"; the file was created on Nov. 7, 2025; the size of the file is 15,872 bytes.

TECHNICAL FIELD

The present invention relates to a *Corynebacterium glutamicum* mutant strain having improved L-glutamic acid productivity and a method of producing L-glutamic acid using the same, and particularly, to a *Corynebacterium glutamicum* mutant strain having increased L-glutamic acid productivity due to a mechanosensitive ion channel gene derived from a *Corynebacterium* sp. strain, which has been introduced therein, a method for constructing the same, and a method of producing L-glutamic acid using the same.

BACKGROUND ART

L-glutamic acid is a representative amino acid that is produced by microbial fermentation. Monosodium L-glutamate (MSG) may increase the preference of foods such as meat, fish, chicken, vegetables, sauces, soups and seasonings by balancing and harmonizing the overall taste of the food, may enhance the taste of low-salt foods having a salt content reduced up to 30%, and thus is widely used as a household seasoning and a seasoning for the production of processed food.

In brief, regarding the pathway of L-glutamic acid fermentation, glucose mainly undergoes the glycolytic pathway (EMP), but a portion thereof is metabolized into two pyruvic acid molecules through the hexose monophosphate pathway (HMP). Among these molecules, one molecule combines with $CO_2$ to form oxaloacetic acid, and the other molecule combines with acetyl CoA from pyruvic acid to form citric acid. Then, oxaloacetic acid and citric acid enter the citric acid cycle (TCA cycle) to form α-ketoglutaric acid. Here, since the TCA cycle lacks the metabolic pathway for the oxidation of α-ketoglutaric acid to succinic acid and isocitrate dehydrogenase and glutamate dehydrogenase are closely involved therein, reductive amino acid synthesis by the oxidation of α-ketoglutaric acid efficiently occurs, thus producing L-glutamic acid.

L-glutamic acid is usually produced by fermentation using mainly *Brevibacterium* sp. or *Corynebacterium* sp. strains and mutant strains thereof. In order to increase the production of L-glutamic acid by microbial culture, a method of regulating the expression of genes involved in L-glutamic acid biosynthesis has been used. For example, a method of increasing the copy number of the gene or regulating the activity of the enzyme in the biosynthesis pathway by modifying the promoter of the gene may be mainly used. Specifically, it was disclosed that L-glutamic acid production was increased by amplifying a specific gene such as pyc gene or fasR (U.S. Pat. No. 6,852,516) or manipulating the promoter region of each of gdh, gltA, icd, pdh and argG genes (U.S. Pat. No. 6,962,805). As such, most of the genes involved in the glutamic acid biosynthesis pathway are already known, and thus it is required to identify a new gene capable of increasing glutamic acid production and to develop a new glutamic acid-producing strain by applying this gene.

Accordingly, the present inventors have identified a new gene that helps L-glutamic acid release, and have constructed a mutant strain by introducing the gene into an L-glutamic acid-producing strain. Also, the present inventors have found that the mutant strain has improved L-glutamic acid productivity, thereby completing the present invention.

DISCLOSURE

Technical Problem

An object of the present invention is to provide a *Corynebacterium glutamicum* mutant strain containing a mechanosensitive ion channel gene derived from a *Corynebacterium* sp. strain and having improved L-glutamic acid productivity.

Another object of the present invention is to provide a method for constructing a *Corynebacterium glutamicum* mutant strain, the method comprising a step of introducing a mechanosensitive ion channel gene derived from a *Corynebacterium* sp. strain.

Still another object of the present invention is to provide a method for producing L-glutamic acid, the method comprising steps of: (i) culturing the *Corynebacterium glutamicum* mutant strain in an L-glutamic acid production medium; and (ii) recovering L-glutamic acid from the cultured mutant strain or the medium in which the mutant strain has been cultured.

Technical Solution

One aspect of the present invention provides a *Corynebacterium glutamicum* mutant strain containing a mechanosensitive ion channel gene derived from a *Corynebacterium* sp. strain and having improved L-glutamic acid productivity.

The present inventors have made efforts to develop a novel *Corynebacterium glutamicum* mutant strain having improved L-glutamic acid productivity, and as a result, have found that, when a mechanosensitive ion channel gene derived from a *Corynebacterium* sp. strain is introduced into an L-glutamic acid-producing *Corynebacterium glutamicum* strain, it helps L-glutamic acid release, thereby significantly improving the L-glutamic acid productivity of the mutant strain.

In the present invention, the "*Corynebacterium* sp. strain" is a strain from which a mechanosensitive ion channel gene to be introduced into a *Corynebacterium glutamicum* strain is derived, and may include any *Corynebacterium* sp. microorganism. Specifically, the *Corynebacterium* sp. strain may be *Corynebacterium glutamicum*, *Corynebacterium crudilactis*, *Corynebacterium deserti*, *Corynebacterium callunae*, *Corynebacterium suranareeae*, *Corynebacterium lubricantis*, *Corynebacterium doosanense*, *Corynebacterium efficiens*, *Corynebacterium uterequi*, *Corynebacterium stationis*, *Corynebacterium pacaense*, *Corynebacterium singulare*, *Corynebacterium humireducens*, *Corynebacterium marinum*, *Corynebacterium halotolerans*, *Corynebacterium spheniscorum*, *Corynebacterium freiburgense*, *Corynebacterium striatum*, *Corynebacterium canis*, *Corynebacterium ammoniagenes*, *Corynebacterium renale*, *Corynebacterium pollutisoli*, *Corynebacterium imitans*,

*Corynebacterium caspium, Corynebacterium testudinoris, Corynebacaterium pseudopelargi,* or *Corynebacterium flavescens.*

In the present invention, the "mechanosensitive ion channel" is a channel present in the cell membranes of bacteria as well as eukaryotes, and is involved in osmotic homeostasis. The gene encoding this mechanosensitive ion channel may be derived from a *Corynebacterium* sp. strain.

Preferably, the gene may be a gene having the nucleotide sequence of SEQ ID NO: 1 derived from *Corynebacterium deserti,* the nucleotide sequence of SEQ ID NO: 2 derived from *Corynebacterium* crudilactis, or the nucleotide sequence of SEQ ID NO: 3 derived from *Corynebacterium callunae.* In addition, the gene may also comprise a nucleotide sequence having a homology of 60% or more, preferably 70% or more, more preferably 80% or more, even more preferably 90% or more, most preferably 95% or more, to the nucleotide sequence of each of SEQ ID NOs: 1 to 3. "Homology of . . . % or more" is determined by comparing two optimally aligned sequences over a comparison region, wherein the portion of the polynucleotide sequence in the comparison region may comprise additions or deletions (i.e., gaps) as compared to the reference sequence (which does not comprise additions or deletions) for optimal alignment of the two sequences. In addition, the gene encoding the mechanosensitive ion channel may have a mutation that occurred naturally or non-naturally (e.g., genetic manipulation, radiation, chemical treatment, etc.), and the function of the gene may be weakened or enhanced by this mutation.

According to one embodiment of the present invention, the mechanosensitive ion channel gene may be encoded by any one of the nucleotide sequences of SEQ ID NOs: 1 to 5.

The nucleotide sequence of SEQ ID NO: 1 may be the nucleotide sequence of a mechanosensitive ion channel gene derived from *Corynebacterium deserti,* the nucleotide sequence of SEQ ID NO: 2 may be the nucleotide sequence of a mechanosensitive ion channel gene derived from *Corynebacterium* crudilactis, and the nucleotide sequences of SEQ ID NOs: 3 to 5 may be the nucleotide sequences of mechanosensitive ion channel genes derived from *Corynebacterium callunae.* Here, the nucleotide sequence of each of SEQ ID NOs: 4 and 5 may encode an amino acid sequence having a substitution of alanine (ALA) or valine (VAL) for leucine (LEU) at position 107 in the amino acid sequence of the mechanosensitive ion channel gene derived from *Corynebacterium callunae.*

The present inventors have presumed that a nucleotide sequence having a homology of 70% or more to the mechanosensitive ion channel gene involved in the release of glutamic acid from *Corynebacterium glutamicum* (a homology of 74% for *Corynebacterium deserti,* 72% for *Corynebacterium* crudilactis, and 70% for *Corynebacterium callunae*) plays the same role in glutamic acid release, and have found that the mutant strain containing the mechanosensitive ion channel gene according to the present invention has significantly improved glutamic acid productivity compared to other glutamic acid-producing strains.

In the present invention, the strain having "increased productivity" means that the strain has L-glutamic acid productivity of the strain is higher than that of a parent strain thereof. The term "parent strain" refers to a wild-type strain or mutant strain to be mutated, and includes a strain that is to be mutated directly or to be transformed with a recombinant vector or the like. In the present invention, the parent strain may be a wild-type *Corynebacterium glutamicum* strain or a strain mutated from the wild-type strain. Preferably, the parent strain may be a *Corynebacterium glutamicum* KCTC 11558BP strain.

The amount of L-glutamic acid produced by the *Corynebacterium glutamicum* mutant strain having increased L-glutamic acid productivity according to an embodiment of the present invention may be at least 5%, specifically 5 to 20% higher than the amount of L-glutamic acid produced by the parent strain. That is, the *Corynebacterium glutamicum* mutant strain can produce 36 to 50 g of L-glutamic acid, preferably 38 to 45 g of L-glutamic acid, per liter of a culture of the strain.

Another aspect of the present invention is to provide a method for constructing the *Corynebacterium glutamicum* mutant strain, the method comprising a step of introducing a mechanosensitive ion channel gene derived from a *Corynebacterium* sp. strain.

The above-described step is a step of transforming the parent strain with a vector containing a polynucleotide encoding the mechanosensitive ion channel gene.

In the present invention, the term "vector" refers to any vehicle for the cloning of and/or transfer of a nucleic acid into a host cell. The vector may be a replicon to which another DNA fragment may be attached so as to bring about the replication of the attached fragment. The term "replicon" refers to any genetic element (e.g., plasmid, phage, cosmid, chromosome, virus) that functions as an autonomous unit of DNA replication in vivo, i.e., capable of replication under its own control. In the present disclosure, the vector is not particularly limited as long as it may replicate in a host, and any vector known in the art may be used. The vector used for the construction of the recombinant vector may be a plasmid, cosmid, virus or bacteriophage in a native state or a recombinant state. Example of a phage vector or cosmid vector that may be used include pWE15, M13, λEMBL3, λEMBL4, λFIXII, λDASHII, λZAPII, λgt10, Δgt11, Charon4A, and Charon21A, and examples of a plasmid vector that may be used include a pDZ vector, and pBR-based, pUC-based, pBluescriptll-based, pGEM-based, pTZ-based, pCL-based and pET-based vectors. A vector that may be used is not particularly limited, and a known expression vector may be used, but is not limited thereto.

In the present disclosure, the term "transformation" means introducing a gene into a host cell so that the gene may be expressed in the host cell. For the transformed gene, it does not matter whether the gene is inserted into the chromosome of the host cell or located outside of the chromosome, as long as the gene may be expressed in the host cell. In the present invention, an example of the transformation method may be an electroporation method (van der Rest et al., Appl. Microbiol. Biotechnol., 52, 541-545, 1999) or the like.

Still another object of the present invention is to provide a method for producing L-glutamic acid, the method comprising steps of: (i) culturing the *Corynebacterium glutamicum* mutant strain in an L-glutamic acid production medium; and (ii) recovering L-glutamic acid from the cultured mutant strain or the medium in which the mutant strain has been cultured.

The culturing may be performed using a suitable medium and culture conditions known in the art, and any person skilled in the art may easily adjust and use the medium and the culture conditions. Specifically, the medium may be a liquid medium, but is not limited thereto. Examples of the culturing method include, but are not limited to, batch culture, continuous culture, fed-batch culture, or a combination thereof.

According to one embodiment of the present invention, the medium should meet the requirements of a specific strain in a proper manner, and may be appropriately modified by a person skilled in the art. For the culture medium for the *Corynebacterium* sp. strain, reference may be made to, but not limited to, a known document (Manual of Methods for General Bacteriology, American Society for Bacteriology, Washington D.C., USA, 1981).

According to one embodiment of the present invention, the medium may contain various carbon sources, nitrogen sources, and trace element components. Examples of carbon sources that may be used include: sugars and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These substances may be used individually or as a mixture, but are not limited thereto. Examples of nitrogen sources that may be used include peptone, yeast extract, meat extract, malt extract, corn steep liquor, soybean meal, urea, or inorganic compounds such as ammonium sulfate, ammonium chloride, ammonium phosphate, ammonium carbonate, and ammonium nitrate. The nitrogen sources may also be used individually or as a mixture, but are not limited thereto. Examples of phosphorus sources that may be used include, but are not limited to, potassium dihydrogen phosphate or dipotassium hydrogen phosphate or the corresponding sodium-containing salts. In addition, the culture medium may contain, but is not limited to, metal salts such as magnesium sulfate or iron sulfate, which are required for growth. In addition, the culture medium may contain essential growth substances such as amino acids and vitamins. Moreover, suitable precursors may be used in the culture medium. The medium or individual components may be added to the culture medium batchwise or in a continuous manner by a suitable method during culturing, without being limited thereto.

According to one embodiment of the present invention, the pH of the culture medium may be adjusted by adding compounds such as ammonium hydroxide, potassium hydroxide, ammonia, phosphoric acid and sulfuric acid to the microorganism culture medium in an appropriate manner during the culturing. In addition, during the culturing, foaming may be suppressed using an anti-foaming agent such as a fatty acid polyglycol ester. Additionally, to keep the culture medium in an aerobic condition, oxygen or an oxygen-containing gas (for example, air) may be injected into the culture medium. The temperature of the culture medium may be generally 20° C. to 45° C., for example, 25° C. to 40° C. The culturing may be continued until a desired amount of a useful substance is produced. For example, the culturing time may be 10 hours to 160 hours.

According to one embodiment of the present invention, in the step of recovering L-glutamic acid from the cultured mutant strain and the culture medium, the produced L-glutamic acid may be collected or recovered from the medium using a suitable method known in the art depending on the culture method. Examples of the method for collecting or recovering L-glutamic acid include, but are not limited to, centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity and size exclusion).

According to one embodiment of the present invention, the step of recovering L-glutamic acid may be performed by centrifuging the culture at a low speed to remove biomass and separating the obtained supernatant through ion-exchange chromatography.

According to one embodiment of the present disclosure, the step of recovering L-glutamic acid may include a process of purifying L-glutamic acid.

Advantageous Effects

Since the *Corynebacterium glutamicum* mutant strain according to one embodiment of the present invention is a strain into which the mechanosensitive ion channel gene derived from a *Corynebacterium* sp. strain has been introduced, it can produce L-glutamic acid in an improved yield due to enhancement of glutamic acid release. Thus, when the mutant strain is used, it is possible to more effectively produce L-glutamic acid.

MODE FOR INVENTION

Hereinafter, the present invention will be described in more detail. However, these descriptions are provided for illustrative purposes only to aid in the understanding of the present invention, and the scope of the present invention is not limited by these illustrative descriptions.

Example 1. Construction of *Corynebacterium glutamicum* Mutant Strains 1-1. Construction of Vector into which Mechanosensitive Ion Channel Gene Derived from *Corynebacterium deserti* has been Introduced In order to introduce the mechanosensitive ion channel gene mscS1, chromosomal DNA was isolated and purified from *Corynebacterium deserti* GIMN1.010. Then, using the purified DNA as a template, PCR amplification was performed using a set of primers 3 and 4 in Table 1 below for 30 cycles, each consisting of 95° C. for 30 sec, 58° C. for 30 sec, and 72° C. for 2 min.

The amplified gene was amplified by PCR using a set of primers 1 and 2 and a set of primers 5 and 6 shown in Table 1 below, which recognized the position within the vector into which the gene was to be inserted, for 30 cycles, each consisting of 95° C. for 30 sec, 58° C. for 30 sec, and 72° C. for 2 min. Bands of about 1,500 bp, 1,600 bp and 1,500 bp, respectively, were confirmed by electrophoresis of the PCR products.

Figure 1:
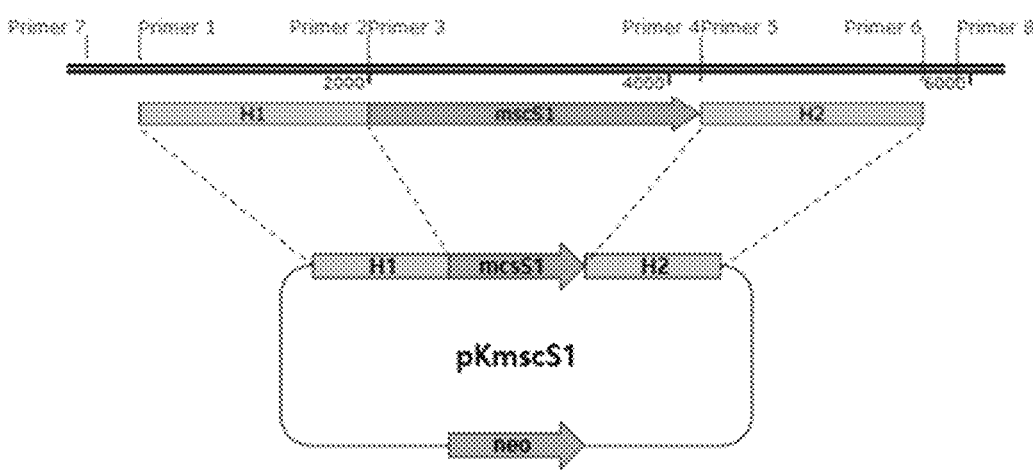
FIG. 1 shows the structure of a pKmscS1 vector containing a mechanosensitive ion channel gene derived from a *Corynebacterium deserti* strain.

Each purified PCR product (mscS1 gene and vector) was then used as a template for crossover polymerase chain reaction (PCR) and amplified again by a crossover PCR technique (Bacteriol., 179: 6228-6237, 1997) using a set of primers 1 and 6 shown in Table 1 below. Next, the 4.6-kb PCR product was purified, digested with BamHI restriction enzyme (Takara, Japan), and then cloned into a pK19mobSacB vector (Gene, 145: 69-73, 1994) digested with the same restriction enzyme, thereby constructing a pKmscS1 vector for introduction of the mscS1 gene (FIG. 1).

TABLE 1

| Primer | Nucleotide sequence (5' → 3') | SEQ ID NO |
|---|---|---|
| Primer 1 | CGCGGATCCTCTGCCTTGCTTGCCTTGGT | 6 |
| Primer 2 | CGGCAGTCCTAAAATCATGAGCCAAGATT AGCGCTG | 7 |
| Primer 3 | CAGCGCTAATCTTGGCTCATGATTTTAGG ACTGCCG | 8 |
| Primer 4 | ACGTCTGTAATCAGCGTCTTATGGGATGG ACGTTGG | 9 |
| Primer 5 | CCAACGTCCATCCCATAAGACGCTGATTA CAGACGT | 10 |
| Primer 6 | CGCGGATCCCCGTTGCCTGGGAGAGAAAG | 11 |
| Primer 7 | GGTGGTGAGTTCCTGGTT | 12 |
| Primer 8 | GTCAACTTCGCCTTCCTG | 13 |

1-2. Construction of Vector into which Mechanosensitive Ion Channel Gene Derived from *Corynebacterium* Crudilactis has been Introduced A pKmscS2 vector for introduction of the mscS2 gene was constructed in the same manner as in Example 1-1, except that *C. crudilactis* strain JZ16 was used instead of *Corynebacterium deserti* and the primers shown in Table 2 below were used.

TABLE 2

| Primer | Nucleotide sequence (5' → 3') | SEQ ID NO |
|---|---|---|
| Primer 1 | CGCGGATCCTCTGCCTTGCTTGCCTTGGT | 6 |
| Primer 2 | GCGTTCACCTAAAATCATGAGCCAAGATT AGCGCTG | 14 |
| Primer 3 | CAGCGCTAATCTTGGCTCATGATTTTAGG TGAACGC | 15 |
| Primer 4 | ACGTCTGTAATCAGCGTCTTATGGGGTGG ACATTGG | 16 |
| Primer 5 | CCAATGTCCACCCCATAAGACGCTGATTA CAGACGT | 17 |
| Primer 6 | CGCGGATCCCCGTTGCCTGGGAGAGAAAG | 11 |
| Primer 7 | GGTGGTGAGTTCCTGGTT | 12 |
| Primer 8 | GTCAACTTCGCCTTCCTG | 13 |

1-3. Construction of Vector into which the Mechanosensitive Ion Channel Gene Derived from *Corynebacterium callunae* has been Introduced A pKmscS3 vector for introduction of the mscS3 gene was constructed in the same manner as in Example 1-1, except that *C. callunae* DSM 20147 was used instead of *Corynebacterium deserti* and the primers shown in Table 3 below were used.

TABLE 3

| Primer | Nucleotide sequence (5' → 3') | SEQ ID NO |
|---|---|---|
| Primer 1 | CGCGGATCCTCTGCCTTGCTTGCCTTGGT | 6 |
| Primer 2 | ACCTCTCTATGACCTCTAGAGAGCCAAGA TTAGCGCTGAA | 18 |
| Primer 3 | TTCAGCGCTAATCTTGGCTCTCTAGAGGT CATAGAGAGGT | 19 |
| Primer 4 | ACACGTCTGTAATCAGCGTCATCCCTACT GGGTGGACGTA | 20 |
| Primer 5 | TACGTCCACCCAGTAGGGATGACGCTGAT TACAGACGTGT | 21 |
| Primer 6 | CGCGGATCCCCGTTGCCTGGGAGAGAAAG | 11 |
| Primer 7 | GGTGGTGAGTTCCTGGTT | 12 |
| Primer 8 | GTCAACTTCGCCTTCCTG | 13 |

1-4. Construction of Vector into which Amino Acid Residue Mutation of Mechanosensitive Ion Channel Gene Derived from *Corynebacterium callunae* has been Introduced In order to substitute the amino acid residue at position 107 in the amino acid sequence of the mechanosensitive ion channel gene mscS3 and introduce the gene, chromosomal DNA was isolated and purified from *Corynebacterium callunae* DSM 20147. Then, using the purified DNA as a template, PCR amplification was performed using a set of primers 1 and 2 and a set of primers 3 and 4 shown in Table 4 below for 30 cycles, each consisting of 95° C. for 30 sec, 58° C. for 30 sec, and 72° C. for 2 min.

Figure 2:
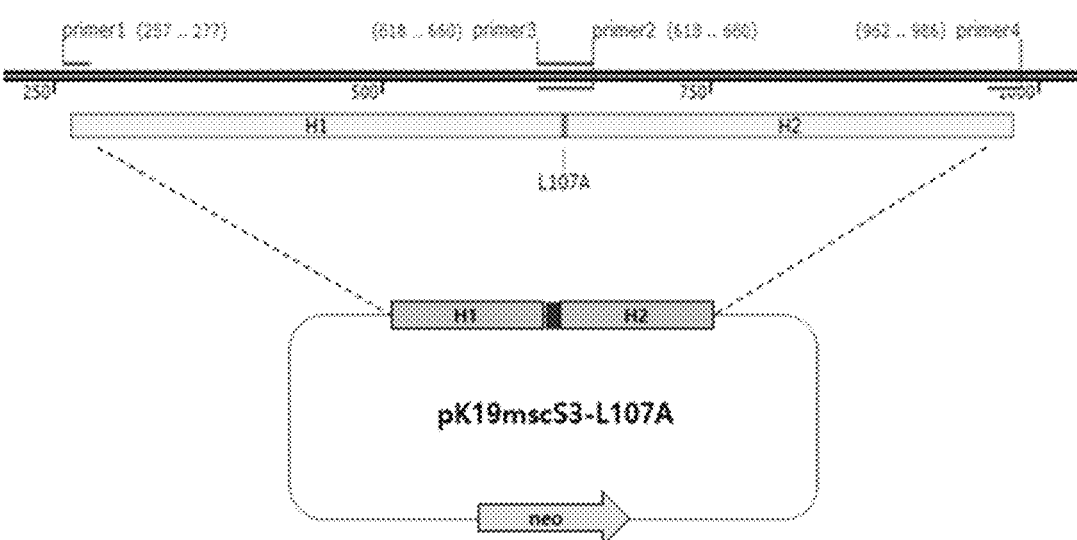
FIG. 2 shows the structure of a pKmscS3-L107A vector containing a mechanosensitive ion channel gene encoding an amino acid sequence having a substitution of alanine (ALA) for the amino acid residue leucine (LEU) at position 107 in the amino acid sequence of a mechanosensitive ion channel gene derived from a *Corynebacterium callunae* strain.

Each purified PCR product (mscS3 gene and vector) was then used as a template for crossover polymerase chain reaction (PCR) and amplified again by a crossover PCR technique (Bacteriol., 179: 6228-6237, 1997) using a set of primers 1 and 4 shown in Table 4 below. Next, the 718-bp PCR product was purified, digested with BamHI restriction enzyme (Takara, Japan), and then cloned into a pK19mobSacB vector (Gene, 145: 69-73, 1994) digested with the same restriction enzyme, thereby constructing a pKmscS3-L107A vector for introduction of a substitution mutation of alanine for the leucine residue at position 107 in the amino acid sequence of the mscS3 gene (FIG. 2).

TABLE 4

| Primer | Nucleotide sequence (5' → 3') | SEQ ID NO |
|---|---|---|
| Primer 1 | CGCGGATCCGGCAGCTCTCAAAGT | 22 |
| Primer 2 | GCGATGATGGATTGCGCGCCtgcACCAA TGGCCGCAGAGGCAA | 23 |
| Primer 3 | TTGCCTCTGCGGCCATTGGTgcaGGCGC GCAATCCATCATCGC | 24 |
| Primer 4 | CGCGGATCCCAGCGATATCTTCTTGGGC | 25 |
| Primer 5 | GGTGGTGAGTTCCTGGTT | 12 |
| Primer 6 | GTCAACTTCGCCTTCCTG | 13 |

1-5. Construction of Vector into which Amino Acid Residue Mutation in Mechanosensitive Ion Channel Gene Derived from *Corynebacterium callunae* has been Introduced A pKmscS3-L107V vector for introduction of a substitution mutation of valine for the leucine residue at position 107 in the amino acid sequence of the mscS3 gene was constructed in the same manner as in Example 1-4, except that the primers shown in Table 5 below were used instead of the primers in Example 1-4.

TABLE 5

| Primer | Nucleotide sequence (5' → 3') | SEQ ID NO |
|---|---|---|
| Primer 1 | CGCGGATCCGGCAGCTCTCAAAGT | 22 |
| Primer 2 | TTGCCTCTGCGGCCATTGGTgttGGCGC GCAATCCATCATCGC | 26 |
| Primer 3 | GCGATGATGGATTGCGCGCCaacACCAA TGGCCGCAGAGGCAA | 27 |
| Primer 4 | CGCGGATCCCAGCGATATCTTCTTGGGC | 25 |
| Primer 5 | GGTGGTGAGTTCCTGGTT | 12 |
| Primer 6 | GTCAACTTCGCCTTCCTG | 13 |

1-6. Transformation of *Corynebacterium glutamicum* KCTC11558BP Strain and Construction of Mutant Strains As a method for transformation of the *Corynebacterium glutamicum* KCTC 11558BP strain, an electrocompetent cell preparation method, a modification of the method of van der Rest, was used.

First, the *Corynebacterium glutamicum* KCTC 11558BP strain was cultured in 100 ml of a 2YT medium (16 g/l tryptone, 10 g/l yeast extract, 5 g/l sodium chloride) supplemented with 2% glucose, and 1 mg/ml of isonicotinic acid hydrazine and 2.5% glycine were added to the same medium free of glucose. Then, the seed culture medium was inoculated to reach an $OD_{610}$ value of 0.3, and then cultured for at 18° C. and 180 rpm for 12 to 16 hours until the $OD_{610}$ value reached 1.2 to 1.4. After keeping on ice for 30 minutes, centrifugation was performed at 4,000 rpm at 4° C. for 15 minutes. Thereafter, the supernatant was discarded and the precipitated *Corynebacterium glutamicum* KCTC 11558BP strain was washed 4 times with a 10% glycerol solution and finally re-suspended in 0.5 ml of a 10% glycerol solution, thereby preparing competent cells. Electroporation was performed using a Bio-Rad electroporator. The prepared competent cells and each of the constructed pKmscS1, pKmscS2, pKmscS3, pKmscS3-L107A and pKmscS3-L107V vectors were placed in an electroporation cuvette (0.2 mm), followed by electroporation under the conditions of 2.5 kV, 200 n and 12.5 µF. Immediately after completion of the electroporation, 1 ml of a regeneration medium (containing 18.5 g/l brain heart infusion powder, and 0.5 M sorbitol) was added to the cells which were then heat-treated at 46° C. for 6 minutes. Next, the cells were cooled at room temperature, transferred into a 15-ml cap tube, incubated at 30° C. for 2 hours, and plated on a selection medium (containing 5 g/l tryptone, 5 g/l NaCl, 2.5 g/l yeast extract, 18.5 g/l brain heart infusion powder, 15 g/l agar, 91 g/l sorbitol, and 20 µg/l kanamycin). The cells were cultured at 30° C. for 72 hours, and the generated colonies were cultured in BHI medium until a stationary phase to induce secondary recombination. Then, the cells were diluted to 10-5 to 10-7 cells, and plated on an antibiotic-free plate (containing 10% sucrose), and strains having no kanamycin resistance and capable of growing in the medium containing 10% sucrose were selected. The selected colonies were confirmed to be *Corynebacterium glutamicum* mutant strains (IS1, IS2 and IS3) into which the mscS1, mscS2 and mscS3 genes have been introduced, respectively, using a set of primers 7 and 8 shown in each of Tables 1 to 3 above. In addition, the selected colonies were confirmed to be *Corynebacterium glutamicum* mutant strains (IS3-A and IS3-V) into which the mscS3-L107A and mscS3-L107V genes have been introduced, respectively, using a set of primers 5 and 6 shown in each of Tables 4 and 5 above.

Experimental Example 1. Comparison of L-Glutamic Acid Productivity Between Mutant Strains L-glutamic acid productivity was compared between the mutant strains (IS1, IS2 and IS3), which were constructed in Example 1 above and into which the mscS1, mscS2 and mscS3 genes have been introduced, respectively, and the patent strain *Corynebacterium glutamicum* KCTC 11558BP strain.

Each of the mutant strains and the parent strain was plated on an active plate medium (pH 7.5) having the composition shown in Table 6 below and was cultured at 30° C. for 24 hours. Thereafter, 10 mL of a flask medium (pH 7.6) having the composition shown in Table 7 below was placed in a 100-ml flask and inoculated with a loop of each of the strains cultured in the plate medium, followed by culturing at 30° C. and 200 rpm for 48 hours. After completion of culturing, the amount of L-glutamic acid in each of the cultures was measured, and the results are shown in Table 8 below.

TABLE 6

| Component | Content |
|---|---|
| Glucose | 5 g/L |
| Yeast extract | 10 g/L |
| Urea | 3 g/L |
| $KH_2PO_4$ | 1 g/L |
| Biotin | 2 µg/L |
| Soybean hydrolysate | 0.1% v/v |
| Leucine | 50 mg/L |
| Agar | 20 g/L |

TABLE 7

| Component | Content |
|---|---|
| Glucose | 70 g/L |
| $MgSO_4 \cdot 7H_2O$ | 0.4 g/L |
| Urea | 2 g/L |
| $KH_2PO_4$ | 1 g/L |
| Soybean hydrolysate | 1.5% v/v |
| $(NH_4)_2SO_4$ | 5 g/L |
| $FeSO_4 \cdot 7H_2O$ | 10 mg/L |
| $MnSO_4 \cdot 5H_2O$ | 10 mg/L |
| Thiamin-HCl | 200 µg/L |
| Biotin | 2 µg/L |
| Calcium carbonate | 50 g/L |

TABLE 8

| | Glutamic acid production (g/L) |
|---|---|
| Parent strain (KCTC 11558BP) | 35.3 |
| Mutant strain (IS1) | 38.2 |
| Mutant strain (IS2) | 37.9 |
| Mutant strain (IS3) | 38.4 |

As shown in Table 8 above, it was confirmed that the L-glutamic acid productivities of the *Corynebacterium glutamicum* mutant strains IS1, IS2 and IS3 into which the *C. deserti*-derived mscS1 gene, the *C. crudilactis*-derived mscS2 gene and the *C. callunae*-derived mscS3 gene have been introduced, respectively, increased by about 8%, 7% and 9%, respectively, compared to the L-glutamic acid productivity of the parent strain *Corynebacterium glutamicum* KCTC 11558BP strain into which none of the genes has been introduced.

Experimental Example 2. Comparison of L-Glutamic Acid Productivity with Those of Mutant Strains Having Amino Acid Residue Substitution L-glutamic acid productivity was compared between the mutant strains IS3, IS3-A and IS3-V, which were constructed in Example 1 above and into which the mscS3, mscS3-L107A and mscS3-L107V genes have been introduced, respectively, and the patent strain *Corynebacterium glutamicum* KCTC 11558BP strain.

The strains were cultured in the same manner as in Example 1, the amount of L-glutamic acid in each of the cultures was measured, and the results are shown in Table 9 below.

TABLE 9

|  | Glutamic acid production (g/L) |
| --- | --- |
| Parent strain (KCTC 11558BP) | 35.3 |
| Mutant strain (IS3) | 38.4 |
| Mutant strain (IS3-A) | 39.7 |
| Mutant strain (IS3-V) | 36.8 |

As shown in Table 9 above, it was confirmed that the L-glutamic acid productivities of the *Corynebacterium glutamicum* mutant strains IS3, IS3-A and IS3-V increased by about 9%, 12% and 4%, respectively, compared to that of the patent strain *Corynebacterium glutamicum* KCTC 11558BP strain.

In particular, it could be seen that, in the case (IS3-A) in which the amino acid residue leucine at position 107 was substituted with alanine, the L-glutamic acid productivity increased compared to that in the case (IS3) in which the amino acid residue leucine was not substituted or in the case (IS3-V) in which the amino acid residue leucine was substituted with valine, suggesting that the amino acid residue at position 107 in the amino acid sequence of the mscS3 gene derived from *C. callunae* is an important position involved in glutamic acid productivity.

So far, the present invention has been described with reference to the embodiments. Those of ordinary skill in the art to which the present invention pertains will appreciate that the present invention may be embodied in modified forms without departing from the essential characteristics of the present invention. Therefore, the disclosed embodiments should be considered from an illustrative point of view, not from a restrictive point of view. The scope of the present invention is defined by the claims rather than the foregoing description, and all differences within the scope equivalent thereto should be construed as being included in the present invention.

---

The invention claimed is:

1. A *Corynebacterium glutamicum* mutant strain having improved L-glutamic acid productivity compared to its parent strain, wherein the *Corynebacterium glutamicum* mutant strain contains a mechanosensitive ion channel gene derived from one strain selected from the group consisting of *Corynebacterium deserti, Corynebacterium crudilactis*, and *Corynebacterium callunae*, and wherein the mechanosensitive ion channel gene is encoded by any one of the nucleotide sequences of SEQ ID NOs: 1 to 5.

2. A method for constructing the *Corynebacterium glutamicum* mutant strain of claim 1, the method comprising a step of introducing into a parent *C. glutamicum* strain a mechanosensitive ion channel gene derived from one strain selected from the group consisting of *Corynebacterium deserti, Corynebacterium crudilactis*, and *Corynebacterium callunae*, wherein the mechanosensitive ion channel gene is encoded by any one of the nucleotide sequences of SEQ ID NOs: 1 to 5.

3. A method for producing L-glutamic acid, the method comprising steps of:

(i) culturing the *Corynebacterium glutamicum* mutant strain of claim 1 in an L-glutamic acid production medium; and (ii) recovering L-glutamic acid from the cultured mutant strain or the medium in which the mutant strain has been cultured.

\* \* \* \* \*

SEQUENCE LISTING

```
<160>  NUMBER OF SEQ ID NOS: 27

<210>  SEQ ID NO 1
<211>  LENGTH: 1635
<212>  TYPE: DNA
<213>  ORGANISM: Artificial Sequence
<220>  FEATURE:
<223>  OTHER INFORMATION: Corynebacterium deserti GIMN1.010

<400>  SEQUENCE: 1 atgattttag gactgccggt taggtacatt ctctattcat tgtggaattg gatcgtcgag      60
actggccttg acctcgcaat tatcctggtt ttagcctttt taatcccacg aatcggcagg     120
ctcgccatgc gagtgatcaa gcgtcgcgtg gaagaaaacg cagatgctga cacgtcgaaa     180
aaccagctgg cttttgctgg cgtgggtgtc tatatcgtgc agattgttgc gttcttcctg     240
ctagttgtcg ccgctctgca gactgtcggc ttgtcgttgg caggtgcagc aattcctgcc     300
acgatcgcat cagctgccat tggtcttggt gcacaatcca tagtcgcgga cttcttggct     360
ggctttttca tcctcacgga aaagcaattc ggtgtgggtg actgggtgcg ctttgaagga     420
aatggcgtgg tggttgaagg taccgtcatt gaaataacca tgcgcgcaac aaaaatccgc     480
accatctcgc aagagacagt catcatccca aattccacgg cgaaggtgtg catcaacaat     540
tccaacaact ggtcgcgtgc cgtggtcatc atgccgattc ccctgcttgg ctcggaaaac     600
atcagcgatg tcatcacgcg ttcagaagct gccactcgcc gcgcgttaga gcaggagaag     660
atcgcaccgg aaatcctcgg cgaactcgat gttcacccgg ccgtcgatgt cactcccca     720 accgtcgtcg gtatgccgtg gacagtctcc atgcgttttc ttgtgcaagt taccgccggc     780
aaccagtggc tcgtcgaacg cgcaatccgc accgaaatca tcagcgaatt ctgggaggaa     840
```

-continued

```
tacggcagcg caaccacaac gacgggtgcg ctcatcgaca ccctcaacgt cagccacgag      900
gtaccgaaag aaaaaccgct tttcgacgcc caccccatc ccttggccga caattctcca      960
aaggctctca ctgaacccaa gccggacgcg gccgccactg tggcatcgct tgccgcctcc     1020
tcaatcgatg atcctgatcc tgtatccacc aagctaagtc ctggaaatcc agaaacagcc     1080
cttgattccg aggttttgga acaagaagta cgggacgagg atgacccagc gaaggaagaa     1140
tccgacaaag atcattctct gcgttcattc ttccgtactg attactaccc caagcgttgg     1200
caaaagattt tatctttggg cggtcgcgta cgcatgagca cctcacttct attggtggtc     1260
ctcggtagct tgctgttact taaaggcatg acagtggaaa ccggggacaa ctggcagggc     1320
tccagcggat ggcttgcgcc gacgtcgcaa acaaccgggg aaaccattcc accaacaacc     1380
accccgttag agacgtttac tcccacgcct gaacctttca caccggaagt gattccgacg     1440
gagtcaagcg tcgatacgca gcctgaaacc tggaaccagg aaaccggcac cccgccgact     1500
gccggtgcca cctccgagcc aaccgagcag acgcctcaaa cacctcagac gacgccggct     1560
acaacctcac aggccacaac gacctcagca gcaccaacag cgaatgtgca gacaactgcg     1620
ccaacgtcca tccca                                                     1635
```

```
<210> SEQ ID NO 2
<211> LENGTH: 1566
<212> TYPE: DNA
<213> ORGANISM: Artificial Sequence
<220> FEATURE:
<223> OTHER INFORMATION: Corynebacterium crudilactis strain JZ16

<400> SEQUENCE: 2
```

```
atgattttag gtgaacgcat ctctttcctt ctttattcat tgtggaattg gattacaaat       60
acaggcattg accttgcaat catcctggtt cttggctttt taatccctcg tttcggccgg      120
attggcatgc ggattatcaa acgccgagtg gaatccaccg ccgatactga cacgaccaaa      180
aaccaactcg cctttgcggg cgtaggcctt tatatcgcac aaatcgtggc attttttcatg     240 cttgcaattg cagcgatgca gctctttggt ttctctctgg caggtgccgc catccccgcc     300
accattgctt ctgctgccat tggtctaggc gcgcaatcca tcgttgcgga tttcttggct     360 ggattttca tcctgacgga aaaacaattt ggtgtaggtg actgggtgcg cttcgaaggc     420
aacggcatca tcgttgaagg cactgtcatt gaaatcacca tgcgtgccac aaaaatccgc     480
acgattgctc aacaaacggt gatcatccct aactccacgg ccaaggtgtg cattaataac     540
tccaacagct ggtcgcgtgc cgttgtgctc atgccgattc cgatgcttgg ttcagacaac     600
atcactgatg ttattgcacg ttctgaagct gcgactcgtc gtgcacttac gcaggaaata     660
atcgcacctg agatcttggg cgagcttgat gtgcaccccg ccatcgatgt cacgccgcct     720
tctgtcgttg gcatgccctg gatggtgacc atgcgtttcc tcgtccaggt caccgcaggt     780
aatcaatggc ttgtcgaacg cgctatccgc accgaaatca tcagcgaatt ttgggaagaa     840
tatggcagcg ccaccaccac atccggtacg ctgatcgatt ccctcagcgt ggttcaggaa     900
aagaatccgc ttatcgacgc ctctcccaac gctttgcagg aaccgaagcc ggaagctgcc     960
gcgacggtcg catcgctagc agcatcatct aacgatgacg ctgctaatac agtgatcagt    1020
ccaggaaatc cagaaaaggg tcttgattcc gaggtgatgg aacaggagct ttccgttgaa    1080
gaagatacgc ccgaggaaca cgcttctctg caaaagtttt tccgtaccga tttctacccc    1140
aagcgttggc aaaagatctt gtccctggga ggccgcgtcc gcatgagtac gtccctactg    1200
```

-continued cttgctgcat taatggtgtt gtcgctgacc aaggtgttga tgattgaacc taatgaaaat      1260
tggcaaaatt ccactggccg cttcgctccg caatcaacca caaccacttc tgaaactcct      1320
acgcagctac cgtcaagctc gatagtttcc cccagcgtgc cggtgtcccc aacggtggag      1380
tcaagcgtcg aaacgcagcc tgaaaccgca acctcccagc cccgtagcac cgctgagcaa      1440
accgaggagc ctacggagga gcagccatca accacaccat caacgacggt tccagaaacc      1500
acgccgcaga cacccgaaac ctcctctcca gcccaagaaa cagcaacacc aatgtccacc      1560
ccataa                                                                 1566

<210> SEQ ID NO 3
<211> LENGTH: 1614
<212> TYPE: DNA
<213> ORGANISM: Artificial Sequence
<220> FEATURE:
<223> OTHER INFORMATION: Corynebacterium callunae DSM 20147

<400> SEQUENCE: 3
atgcccattc ccgtgcttta tttactttca cagttttggt cctgggttgt tgaaaccgga        60
ctagatcttg cgctgatttt ggtattggca tttcttattc cccgcattgg tcgttttttct      120 atgcgggtta ttaagcaccg tattgaaaac aatgcagatg ccgataccac caaaaaccaa       180
ctagcctttg ccggcgttgg agtttatatc gcgcaaataa tcgcctttttt tattcttatt      240 gtttcggccc tgcaacagct cgggtttttca ctagccggcg cggcgattcc cgcgacagtt      300
gcctctgcgg ccattggtct tggcgcgcaa tccatcatcg ccgatttcct cgccggattt      360
tttatcctca cggaaaaaca attcggccgtg ggtgactggg tgcgctttga aggcaatggc      420
atcgtggtgg aaggcaccgt tattgaaatc acgatgcgtg ccacgcgcat tcgaaccatt      480
agccaagaga cggtaataat cccgaattcc acggccaagg tctgcattaa caactccaat      540
aactggtcgc gcgcggtggt tgtcatcccg atcccaatgc tgggttccga gaatatttct      600
gaggttatta cccgctcgga gcaggcaact cgccgcgcat tggcccaaga agatatcgct      660
gcggaggtac ttggtgagct tgatgtacac ccggcaattg atgtcactcc ccccaccgtt      720
gttggtatgc catggatggt aaccatgcgt ttcttggtgc aggtcaccgc tggtaatcag      780
tggttggttg aacgcgccat ccgcacccaa attattgacg agttctgggc tgagtacggc      840
tctgccacca ccacgtcagg caccctgatt gattcactta acctcgagca tgaggacccc      900
tattataggg gtgtaaaaac cccgcttgtc gacgaaaaac tggagcgaac tggcacccaa      960
ccaaaagctg cagaagacgc cagcatcgta tcgatggcag caagttccaa agatgatcca     1020
gatcccgcca ctgaggtact aagtccaggg aatccagaga aatcccttga cttggaggtg     1080
ccacatgctg aactagaatc cgagaaaccg gcggaagaaa gagccgataa ggatcatttt     1140
atcggtggct ttttccgcac cgattattat ccaaagcgct ggcaaaaagt gttgtccatt     1200
ggtggtcgag tccgtatgac cacctccatc ctgttgctta tcctgggctt tttactgtta     1260
ctcaaaggtt taacggtaca aactagcccg gaatggcagg gctcaaatgg ttggttagct     1320
ccagatactg aaaccacaac tactcaaagc tccatggttg ctcccaccac atcagagtcc     1380
actacaacta ctccaccgca gcgttccagc gtcgaaacgc gctcttctac ctctattcct     1440
gagaccagca cttttagcac cttcgacgag gaaccggcgc ccgcggagca aagctctgca     1500
gcttccacaa ccagccagca gcaacagcaa cagaccacat ctgcgccgac tacacaggag     1560
agcacgccga cctcaacggc acagccacag gcaacagtta cgtccaccca gtag          1614

```
<210> SEQ ID NO 4
<211> LENGTH: 1614
<212> TYPE: DNA
<213> ORGANISM: Artificial Sequence
<220> FEATURE:
<223> OTHER INFORMATION: Corynebacterium callunae DSM 20147 - L107A

<400> SEQUENCE: 4
atgcccattc ccgtgcttta tttactttca cagttttggt cctgggttgt tgaaaccgga      60
ctagatcttg cgctgatttt ggtattggca tttcttattc cccgcattgg tcgtttttct     120
atgcgggtta ttaagcaccg tattgaaaac aatgcagatg ccgataccac caaaaaccaa     180
ctagcctttg ccggcgttgg agtttatatc gcgcaaataa tcgccttttt tattcttatt     240
gtttcggccc tgcaacagct cgggttttca ctagccggcg cggcgattcc cgcgacagtt     300
gcctctgcgg ccattggtgc aggcgcgcaa tccatcatcg ccgatttcct cgccggattt     360
tttatcctca cggaaaaaca attcggcgtg ggtgactggg tgcgctttga aggcaatggc     420
atcgtggtgg aaggcaccgt tattgaaatc acgatgcgtg ccacgcgcat tcgaaccatt     480
agccaagaga cggtaataat cccgaattcc acggccaagg tctgcattaa caactccaat     540
aactggtcgc gcgcggtggt tgtcatcccg atcccaatgc tgggttccga gaatatttct     600
gaggttatta cccgctcgga gcaggcaact cgccgcgcat tggcccaaga agatatcgct     660
gcggaggtac ttggtgagct tgatgtacac ccggcaattg atgtcactcc ccccaccgtt     720
gttggtatgc catggatggt aaccatgcgt ttcttggtgc aggtcaccgc tggtaatcag     780
tggttggttg aacgcgccat ccgcacccaa attattgacg agttctgggc tgagtacggc     840
tctgccacca ccacgtcagg caccctgatt gattcactta acctcgagca tgaggacccc     900
tattataggg gtgtaaaaac cccgcttgtc gacgaaaaac tggagcgaac tggcaccccaa    960 ccaaaagctg cagaagacgc cagcatcgta tcgatggcag caagttccaa agatgatcca    1020
gatcccgcca ctgaggtact aagtccaggg aatccagaga aatcccttga cttggaggtg    1080
ccacatgctg aactagaatc cgagaaaccg gcggaagaaa gagccgataa ggatcatttt    1140
atcggtggct tttttccgcac cgattattat ccaaagcgct ggcaaaaagt gttgtccatt    1200
ggtggtcgag tccgtatgac cacctccatc ctgttgctta tcctgggctt tttactgtta    1260
ctcaaaggtt taacggtaca aactagcccg gaatggcagg gctcaaatgg ttggttagct    1320
ccagatactg aaaccacaac tactcaaagc tccatggttg ctcccaccac atcagagtcc    1380
actacaacta ctccaccgca gcgttccagc gtcgaaacgc gctcttctac ctctattcct    1440
gagaccagca cttttagcac cttcgacgag gaaccggcgc ccgcggagca aagctctgca    1500
gcttccacaa ccagccagca gcaacagcaa cagaccacat ctgcgccgac tacacaggag    1560
agcacgccga cctcaacggc acagccacag gcaacagtta cgtccaccca gtag          1614

<210> SEQ ID NO 5
<211> LENGTH: 1614
<212> TYPE: DNA
<213> ORGANISM: Artificial Sequence
<220> FEATURE:
<223> OTHER INFORMATION: Corynebacterium callunae DSM 20147 - L107V

<400> SEQUENCE: 5
atgcccattc ccgtgcttta tttactttca cagttttggt cctgggttgt tgaaaccgga      60
ctagatcttg cgctgatttt ggtattggca tttcttattc cccgcattgg tcgtttttct     120
atgcgggtta ttaagcaccg tattgaaaac aatgcagatg ccgataccac caaaaaccaa     180
```

-continued

```
ctagcctttg ccggcgttgg agtttatatc gcgcaaataa tcgccttttt tattcttatt      240
gtttcggccc tgcaacagct cgggtttca ctagccggcg cggcgattcc cgcgacagtt       300
gcctctgcgg ccattggtgt tggcgcgcaa tccatcatcg ccgatttcct cgccggattt      360
tttatcctca cggaaaaaca attcggcgtg ggtgactggg tgcgctttga aggcaatggc      420
atcgtggtgg aaggcaccgt tattgaaatc acgatgcgtg ccacgcgcat tcgaaccatt      480
agccaagaga cggtaataat cccgaattcc acggccaagg tctgcattaa caactccaat      540
aactggtcgc gcgcggtggt tgtcatcccg atcccaatgc tgggttccga gaatatttct      600
gaggttatta cccgctcgga gcaggcaact cgccgcgcat tggcccaaga agatatcgct      660
gcggaggtac ttggtgagct tgatgtacac ccggcaattg atgtcactcc ccccaccgtt      720
gttggtatgc catggatggt aaccatgcgt ttcttggtgc aggtcaccgc tggtaatcag      780
tggttggttg aacgcgccat ccgcacccaa attattgacg agttctgggc tgagtacggc      840
tctgccacca ccacgtcagg caccctgatt gattcactta acctcgagca tgaggacccc      900
tattatgggg gtgtaaaaac cccgcttgtc gacgaaaaac tggagcgaac tggcacccaa      960
ccaaaagctg cagaagacgc cagcatcgta tcgatggcag caagttccaa agatgatcca     1020
gatcccgcca ctgaggtact aagtccaggg aatccagaga aatcccttga cttggaggtg     1080
ccacatgctg aactagaatc cgagaaaccg gcggaagaaa gagccgataa ggatcatttt     1140
atcggtggct ttttccgcac cgattattat ccaaagcgct ggcaaaaagt gttgtccatt     1200
ggtggtcgag tccgtatgac cacctccatc ctgttgctta tcctgggctt tttactgtta     1260
ctcaaaggtt taacggtaca aactagcccg gaatggcagg gctcaaatgg ttggttagct     1320
ccagatactg aaaccacaac tactcaaagc tccatggttg ctcccaccac atcagagtcc     1380
actacaacta ctccaccgca gcgttccagc gtcgaaacgc gctcttctac ctctattcct     1440
gagaccagca cttttagcac cttcgacgag gaaccggcgc ccgcggagca aagctctgca     1500
gcttccacaa ccagccagca gcaacagcaa cagaccacat ctgcgccgac tacacaggag     1560
agcacgccga cctcaacggc acagccacag gcaacagtta cgtccaccca gtag          1614
```

```
<210> SEQ ID NO 6
<211> LENGTH: 29
<212> TYPE: DNA
<213> ORGANISM: Artificial Sequence
<220> FEATURE:
<223> OTHER INFORMATION: Primer 1 (table 1)

<400> SEQUENCE: 6
cgcggatcct ctgccttgct tgccttggt                                        29

<210> SEQ ID NO 7
<211> LENGTH: 36
<212> TYPE: DNA
<213> ORGANISM: Artificial Sequence
<220> FEATURE:
<223> OTHER INFORMATION: Primer 2 (table 1)

<400> SEQUENCE: 7
cggcagtcct aaaatcatga gccaagatta gcgctg                                36

<210> SEQ ID NO 8
<211> LENGTH: 36
<212> TYPE: DNA
<213> ORGANISM: Artificial Sequence
<220> FEATURE:
<223> OTHER INFORMATION: Primer 3 (table 1)
```

-continued

<400> SEQUENCE: 8
cagcgctaat cttggctcat gattttagga ctgccg                               36

<210> SEQ ID NO 9
<211> LENGTH: 36
<212> TYPE: DNA
<213> ORGANISM: Artificial Sequence
<220> FEATURE:
<223> OTHER INFORMATION: Primer 4 (table 1)

<400> SEQUENCE: 9
acgtctgtaa tcagcgtctt atgggatgga cgttgg                               36

<210> SEQ ID NO 10
<211> LENGTH: 36
<212> TYPE: DNA
<213> ORGANISM: Artificial Sequence
<220> FEATURE:
<223> OTHER INFORMATION: Primer 5 (table 1)

<400> SEQUENCE: 10
ccaacgtcca tcccataaga cgctgattac agacgt                               36

<210> SEQ ID NO 11
<211> LENGTH: 29
<212> TYPE: DNA
<213> ORGANISM: Artificial Sequence
<220> FEATURE:
<223> OTHER INFORMATION: Primer 6 (table 1)

<400> SEQUENCE: 11
cgcggatccc cgttgcctgg gagagaaag                                       29

<210> SEQ ID NO 12
<211> LENGTH: 18
<212> TYPE: DNA
<213> ORGANISM: Artificial Sequence
<220> FEATURE:
<223> OTHER INFORMATION: Primer 7 (table 1)

<400> SEQUENCE: 12
ggtggtgagt tcctggtt                                                   18

<210> SEQ ID NO 13
<211> LENGTH: 18
<212> TYPE: DNA
<213> ORGANISM: Artificial Sequence
<220> FEATURE:
<223> OTHER INFORMATION: Primer 8 (table 1)

<400> SEQUENCE: 13
gtcaacttcg ccttcctg                                                   18

<210> SEQ ID NO 14
<211> LENGTH: 36
<212> TYPE: DNA
<213> ORGANISM: Artificial Sequence
<220> FEATURE:
<223> OTHER INFORMATION: Primer 2 (table 2)

<400> SEQUENCE: 14
gcgttcacct aaaatcatga gccaagatta gcgctg                               36

<210> SEQ ID NO 15

```
<211> LENGTH: 36
<212> TYPE: DNA
<213> ORGANISM: Artificial Sequence
<220> FEATURE:
<223> OTHER INFORMATION: Primer 3 (table 2)

<400> SEQUENCE: 15
cagcgctaat cttggctcat gattttaggt gaacgc                                   36

<210> SEQ ID NO 16
<211> LENGTH: 36
<212> TYPE: DNA
<213> ORGANISM: Artificial Sequence
<220> FEATURE:
<223> OTHER INFORMATION: Primer 4 (table 2)

<400> SEQUENCE: 16
acgtctgtaa tcagcgtctt atggggtgga cattgg                                   36

<210> SEQ ID NO 17
<211> LENGTH: 36
<212> TYPE: DNA
<213> ORGANISM: Artificial Sequence
<220> FEATURE:
<223> OTHER INFORMATION: Primer 5 (table 2)

<400> SEQUENCE: 17
ccaatgtcca ccccataaga cgctgattac agacgt                                   36

<210> SEQ ID NO 18
<211> LENGTH: 40
<212> TYPE: DNA
<213> ORGANISM: Artificial Sequence
<220> FEATURE:
<223> OTHER INFORMATION: Primer 2 (table 3)

<400> SEQUENCE: 18
acctctctat gacctctaga gagccaagat tagcgctgaa                               40

<210> SEQ ID NO 19
<211> LENGTH: 40
<212> TYPE: DNA
<213> ORGANISM: Artificial Sequence
<220> FEATURE:
<223> OTHER INFORMATION: Primer 3 (table 3)

<400> SEQUENCE: 19
ttcagcgcta atcttggctc tctagaggtc atagagaggt                               40

<210> SEQ ID NO 20
<211> LENGTH: 40
<212> TYPE: DNA
<213> ORGANISM: Artificial Sequence
<220> FEATURE:
<223> OTHER INFORMATION: Primer 4 (table 3)

<400> SEQUENCE: 20
acacgtctgt aatcagcgtc atccctactg ggtggacgta                               40

<210> SEQ ID NO 21
<211> LENGTH: 40
<212> TYPE: DNA
<213> ORGANISM: Artificial Sequence
<220> FEATURE:
<223> OTHER INFORMATION: Primer 5 (table 3)

<400> SEQUENCE: 21
```

```
tacgtccacc cagtagggat gacgctgatt acagacgtgt                           40

<210> SEQ ID NO 22
<211> LENGTH: 24
<212> TYPE: DNA
<213> ORGANISM: Artificial Sequence
<220> FEATURE:
<223> OTHER INFORMATION: Primer 1 (table 4)

<400> SEQUENCE: 22
cgcggatccg gcagctctca aagt                                            24

<210> SEQ ID NO 23
<211> LENGTH: 43
<212> TYPE: DNA
<213> ORGANISM: Artificial Sequence
<220> FEATURE:
<223> OTHER INFORMATION: Primer 2 (table 4)

<400> SEQUENCE: 23
gcgatgatgg attgcgcgcc tgcaccaatg gccgcagagg caa                       43

<210> SEQ ID NO 24
<211> LENGTH: 43
<212> TYPE: DNA
<213> ORGANISM: Artificial Sequence
<220> FEATURE:
<223> OTHER INFORMATION: Primer 3 (table 4)

<400> SEQUENCE: 24
ttgcctctgc ggccattggt gcaggcgcgc aatccatcat cgc                       43

<210> SEQ ID NO 25
<211> LENGTH: 28
<212> TYPE: DNA
<213> ORGANISM: Artificial Sequence
<220> FEATURE:
<223> OTHER INFORMATION: Primer 4 (table 4)

<400> SEQUENCE: 25
cgcggatccc agcgatatct tcttgggc                                        28

<210> SEQ ID NO 26
<211> LENGTH: 43
<212> TYPE: DNA
<213> ORGANISM: Artificial Sequence
<220> FEATURE:
<223> OTHER INFORMATION: Primer 2 (table 5)

<400> SEQUENCE: 26
ttgcctctgc ggccattggt gttggcgcgc aatccatcat cgc                       43

<210> SEQ ID NO 27
<211> LENGTH: 43
<212> TYPE: DNA
<213> ORGANISM: Artificial Sequence
<220> FEATURE:
<223> OTHER INFORMATION: Primer 3 (table 5)

<400> SEQUENCE: 27
gcgatgatgg attgcgcgcc aacaccaatg gccgcagagg caa                       43
```